US00PP16614P3

(12) United States Plant Patent
Carruth

(10) Patent No.: US PP16,614 P3
(45) Date of Patent: Jun. 6, 2006

(54) HYBRID TEA ROSE PLANT NAMED 'WEKHILPURNIL'

(50) Latin Name: *Rosa hybrida*
Varietal Denomination: WEKhilpurnil

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 102 days.

(21) Appl. No.: 10/986,236

(22) Filed: Nov. 11, 2004

(65) Prior Publication Data

US 2006/0101548 P1 May 11, 2006

(51) Int. Cl.
*A01H 5/00* (2006.01)

(52) U.S. Cl. ..... Plt./130; Plt./130

(58) Field of Classification Search ..... Plt./130, Plt./137, 141, 148
See application file for complete search history.

(56) References Cited

U.S. PATENT DOCUMENTS

PP4,671 P 3/1981 Delbard

OTHER PUBLICATIONS

Rose 'Wekhilpurnil', Help Me Find [online] [retrieved on Jun. 6, 2005]. Retrieved on the Internet: <http://www.help-mefind.com/rose/pl.php?n=44164>, 2 pages.*

* cited by examiner

*Primary Examiner*—Anne Marie Grunberg
*Assistant Examiner*—June Hwu
(74) *Attorney, Agent, or Firm*—McKee, Voorhees & Sease, P.L.C.

(57) ABSTRACT

A new variety of Hybrid Tea rose suitable for garden decoration, having flowers of lavender blushed purple coloration.

1 Drawing Sheet

BACKGROUND OF THE INVENTION

This invention relates to a new and distinct variety of Hybrid Tea Rose. The varietal denomination of the new variety is *Rosa hybrida* 'WEKhilpurnil'. It has as an undisseminated seedling of Applicant's creation as its seed parent with the following genetic origin (Blueberry Hill×Stephen's Big Purple) and as its pollen parent the variety known as 'DELnible' (U.S. Plant Pat. No. 4,671).

SUMMARY OF THE INVENTION

Among the features which distinguish the new variety from other presently available and commercial rose cultivars known to the inventor are the following combination of characteristics: its strong citrus-like fragrance, its yellow-green styles and its lavender blushed purple flower coloration. The plant has an upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKhilpurnil' may be asexually propagated by budding or grafting. The budding and grafting successfully occurred on the plant/rootstock *Rosa hybrida* cv. 'Dr. Huey'.

COMPARISON WITH PARENTS

The new rose may be distinguished from its seed parent, an undisseminated seedling of Applicant's creation with the following genetic origin (Blueberry Hill×Stephen's Big Purple), by the following combination of characteristics:

whereas 'WEKhilpurnil' bears large flowers, with about 10.6 to about 12.5 cm in diameter, of lavender blushed purple coloration and double petalage with about 34 to 45 petals, the undisseminated seedling bears significantly smaller flowers, with about 6.4 to about 8.5 cm. in diameter, of deep purple coloration and semi-double petalage with about 19 to 26 petals. The new variety has an upright growing habit, whereas the seed parent has a significantly smaller bushy rounded mature growing habit.

The new variety may be distinguished from its pollen parent, 'DELnible' by the following combination of characteristics: whereas 'WEKhilpurnil' bears flowers with double petalage, about 34 to 45 petals, 'DELnible' bears flowers with significantly lesser petalage, with about 25 to 30 petals. 'WEKhilpurnil' bears many large prickles and some small prickles on its major stems and branches, whereas 'DELnible' bears few large prickles and no small prickles on its major stems and branches. The new variety has an upright medium height growing habit, whereas the pollen parent has a significantly taller upright spreading mature growing habit.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color references and/or values are based upon the Colour Chart of The Royal Horticultural Society of London, England (1966), except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

BOTANICAL DESIGNATION:

The new variety botanical designation is *Rosa hybrida* 'WEKhilpurnil'.

FLOWER

The new variety sometimes bears its flowers singly, usually in clusters of three to five or more per stem. Flowers may be borne in regular rounded clusters on strong medium to long stems (about 46 to about 72 cm.). Outdoors, the plant blooms abundantly and nearly continuously during the growing season. The flowers have a strong citrus blossom fragrance.

BUD

The peduncle is about 5.2 to about 8.6 cm. in length, of average caliper (about 0.3 to about 0.5 cm. in diameter), and usually erect. It is almost entirely smooth, with some stipitate glands and hairs. Peduncle color is between 144A and 148A, sometimes lightly suffused, especially on the side exposed to the sun, with between 187C and 183C.

Before the calyx breaks, the bud is about 1.6 to about 2.3 cm. in diameter at the widest point, about 1.9 to about 2.7 cm. in length, and ovoid to somewhat pointed in shape. The surface of the bud bears some foliaceous appendages and hairs, usually with slender entire foliaceous parts extending beyond the tip of the bud about ¼ or more of its length. Bud color is between 146A and 146B, sometimes lightly suffused, especially on the side exposed to the sun, with between 187B and 183B.

The sepals are about 2.4 to about 4.1 cm. in length and about 0.8 to about 1.4 cm. in width at the widest point. The outer surface color of the sepal is between 146A and 146B, sometimes lightly suffused, especially on the side exposed to the sun, with between 187B and 183B. The inner surface color of the sepal is between 137C and 138A and covered with fine wooly tomentum; sepal margins are lined with some stipitate glands and hairs.

As the petals open (after the calyx breaks), the bud is about 2.1 to about 2.7 cm. in diameter at the widest point, about 2.6 to about 3.5 cm. in length, and ovoid in form. The color of the under surfaces of the newly opened petals is between 69C and 69B, usually strongly suffused, especially on the outermost petals with between 59A and 185A. At the point where the petal attaches, there is a moderately large zone of between 1C and 1D. The color of the upper surfaces of the newly opened petals is between 80D and 78D. At the point where the petal attaches, there is a moderately large zone of between 1C and 1D.

BLOOM

When fully open, the bloom ranges from about 10.6 to about 12.5 cm. in diameter. Petalage is double with about 34 to 45 petals and about 3 to 9 petaloids irregularly arranged. When partially open, the bloom form is moderately high centered to somewhat cupped, and the petals are moderately tightly spiraled to cupped with petal edges somewhat reflexed outward. When fully open, the bloom form is more cupped, and the petals are loosely cupped with petal edges moderately reflexed outward.

PETALOIDS

Petaloids are about 0.9 to about 1.4 cm. in length and about 0.3 to about 0.6 cm. in width at the widest point. Petaloids are shaped moderately oblanceolate to somewhat oblong with rounded apices. The under and upper surface color of the petaloids are similar in coloration to the upper and under surface color of the inner petals of the newly opened flower.

PETALS

The substance of the petals is somewhat heavy and of medium thickness, with upper surfaces somewhat shiny to matte and under surfaces slightly shiny to matte. The outer petals are nearly rounded in shape with rounded apices. The inner petals are nearly rounded in shape with rounded apices. The petals are about 3.5 to about 5.4 cm. in length and about 3.5 to about 6.0 cm. in width at the widest point. Petal margins are entire.

NEWLY OPENED FLOWER

The under and upper surface color of the outer and intermediate petals is between 75C and 75D sometimes moderately blushed toward the petal edges with between 71B and 185C. The blushed coloration is usually more evident on the under side of the outermost petals. At the point where the petal attaches, there is a moderately large zone of near 2D.

The under and upper surface color of the inner petals is between 75C and 73D.

The general tonality of the newly opened flower is between 75C and 75D sometimes moderately blushed toward the petal edges with between 71B and 185C.

THREE DAY OLD FLOWER

The under and upper surface color of the outer and intermediate petals is between 76D and 75D sometimes moderately blushed toward the petal edges with between 71C and 60D. The blushed coloration is usually more evident on the under side of the outermost petals. At the point where the petal attaches, there is a moderately large zone of near 4D.

The under and upper surface color of the inner petals is between 76D and 75D.

The general tonality of the three-day-old flower is between 76D and 75D sometimes moderately blushed toward the petal edges with between 71C and 60D.

On the spent bloom, the petals usually drop off cleanly.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 105) and are arranged regularly about the pistils; a few are mixed with petaloids or tucked in the calyx. The filaments are of medium to long length (about 0.7 to about 1.4 cm.), most with anthers. Filaments are between 2D and 4D in color. The anthers are moderately small to medium for the class and all open approximately at the same time. Anther color is between 20A and 11D when immature and between 164C and 200B at maturity. Pollen is abundant and between 19A and 22B in color.

FEMALE REPRODUCTIVE ORGANS

Pistils vary in number (average about 150). The styles are moderately even, very short in length (about 0.3 to about 0.6 cm.), moderately thin in caliper, and loosely bunched. Stigma color is between 22D and 23D. Style color is between 149D and 150D often lightly suffused near the top with between 53C and 53D. Ovaries are usually all enclosed in the calyx.

Hips have not been observed on this variety when grown in Upland, Calif.

RECEPTACLE

The receptacle is of average length (about 0.6 to about 1.1 cm.) and of average caliper (about 0.7 to about 1.3 cm. in diameter). The receptacle is globular to almost rounded in form. It surface is very smooth with thick fleshy walls. The receptacle color is between 146A and 146B.

FOLIAGE

The compound leaves are usually comprised of three to five or more leaflets and are borne abundantly. The five-leaflet leaves are about 12.1 to about 16.4 cm. in length and about 10.6 to about 15.1 cm. in width at the widest point, moderately leathery to somewhat crisp in texture, and semi-glossy in finish. The terminal leaflets are about 4.7 to about 9.2 cm. in length and about 2.3 to about 5.4 cm. in width at the widest point, shaped moderately ovate to somewhat oval with acute apices and rounded bases. Their margins are usually simply serrate.

The upper surface color of the mature leaf is between 147A and 146B. The under surface color of the mature leaf is between 147B and 146B. The upper surface color of the young leaf is between 146A and 148A, usually heavily suffused with between 187A and 183B. The under surface color of the young leaf is between 146B and 148B, usually heavily suffused with between 187C and 183B.

The rachis is of average size caliper and moderately rough. The upper side is moderately grooved with some hairs and stipitate glands on the edges of the grooves. The under side of the rachis is moderately rough with some stipitate glands and few small prickles. The rachis color is between 146C and 147B.

The stipules are about 1.2 to about 1.9 cm. in length and moderately wide in width (about 0.9 to about 1.5 cm.) with moderately long straight points that usually turn out at an angle of more than 45 degrees and sometimes recurve toward the stem. The stipules color is between 137A and 146B.

The petiole is about 0.8 to about 1.7 cm. in length and about 0.1 to about 0.2 cm in diameter at the widest point. The petiole color is between 146C and 147B.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has an upright medium height growing habit (about 138 to about 154 cm. in height and about 57 to about 72 cm. spread at the widest point), with full branching. It displays moderately vigorous growth and the canes are of moderately heavy caliper for the class.

The color of the major stems is between 146B and 148A. They bear many large prickles that are about 0.6 to about 1.2 cm. in length. The large prickles are almost straight and angled slightly downward with a somewhat long narrow oval base; prickle color is between 166C and 166D. The major stem bears some small prickles of similar shape and coloration.

The color of the branches is between 144A and 148A. They bear many large prickles which are of similar size and shape to the large prickles on the major stems; prickle color is near 160A sometimes suffused near the base with between 184A and 183B. The branches bear some small prickles of similar shape and coloration.

The color of the new shoots is between 146A and 148A often moderately suffused with between 187B and 183B. They bear many large prickles which are of similar size and shape to the large prickles on the major stems; prickle color is between 187B and 183B. The shoots bear some small prickles of similar shape and coloration.

I claim:

1. A new and distinct Hybrid Tea rose plant of the variety substantially as described and illustrated herein.

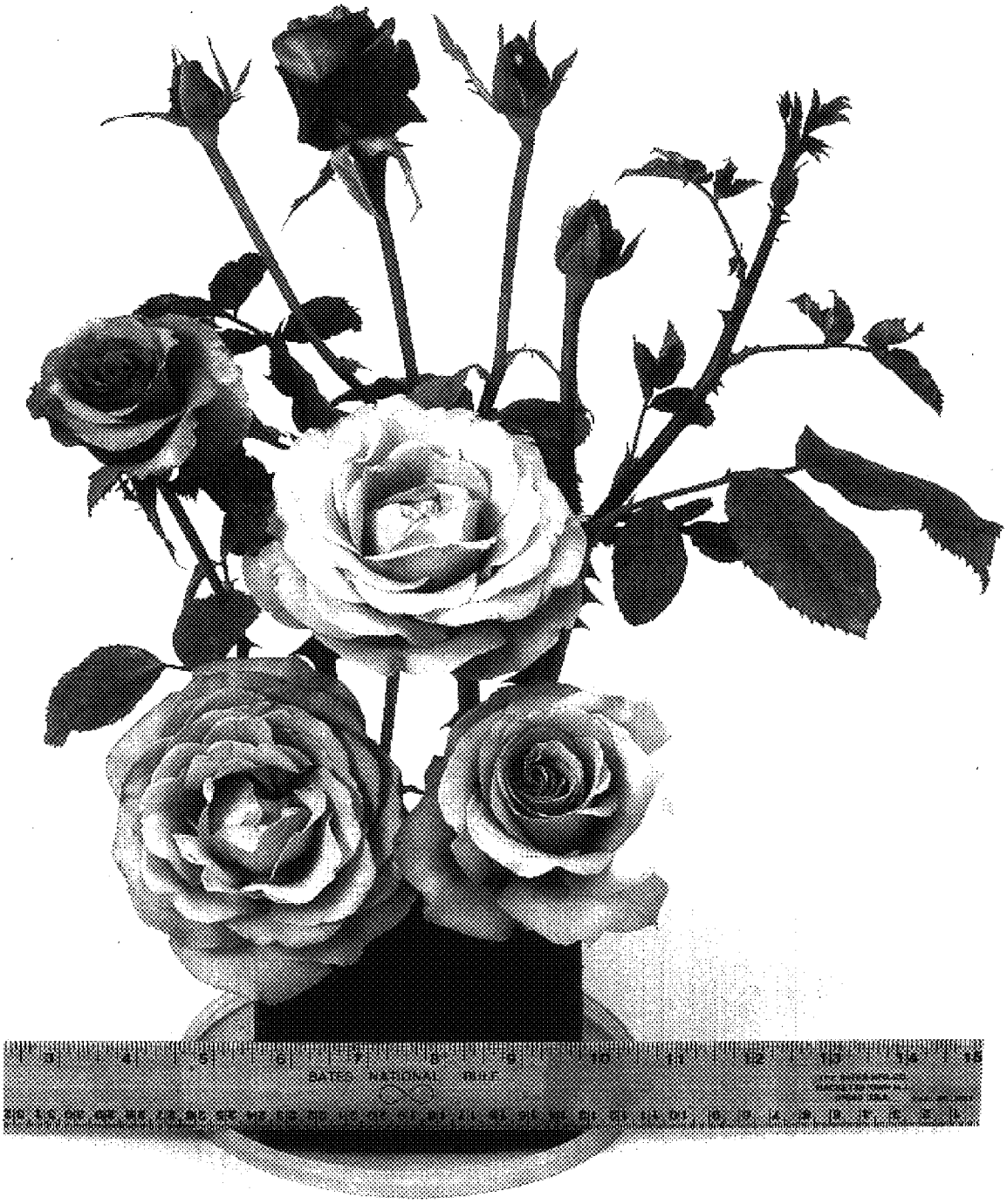

* * * * *